United States Patent [19]

Vora

[11] Patent Number: 4,774,088

[45] Date of Patent: Sep. 27, 1988

[54] METHOD AND ADDITIVES FOR IMPROVING THE QUALITY AND SHELF LIFE OF STORED BLOOD

[75] Inventor: Shobhana Vora, San Diego, Calif.

[73] Assignee: The United States of America as represented by the Deptment of Health and Human Services, Washington, D.C.

[21] Appl. No.: 817,189

[22] Filed: Jan. 8, 1986

[51] Int. Cl.[4] .................... A61K 35/14; A61K 35/18
[52] U.S. Cl. ........................................ 424/101; 435/2
[58] Field of Search ............................. 435/2; 424/101

[56] References Cited

U.S. PATENT DOCUMENTS

| | | | |
|---|---|---|---|
| 3,925,153 | 12/1975 | Laborit | 435/2 |
| 4,112,070 | 9/1978 | Harmening | 424/101 |
| 4,476,221 | 10/1984 | Kane et al. | 435/2 |
| 4,572,899 | 2/1986 | Walker et al. | 435/2 |
| 4,609,372 | 9/1986 | Carmen et al. | 424/101 |

OTHER PUBLICATIONS

Merck Index–ninth edition (1976), p. 1039.

*Primary Examiner*—Sam Rosen
*Attorney, Agent, or Firm*—Browdy and Neimark

[57] ABSTRACT

A method for improving the quality and/or increasing the shelf-life of whole blood and red blood cell concentrates during storage thereof comprising manipulating the activities of the key red cell enzymes involved in the biosynthesis and degradation of 2,3-DPG (DPGM, DPGP, PGP) and in regulation of glycolysis (PK and PFK). The enzymes are manipulated, i.e. activated or inhibited, either singly or in combination. Such manipulations are achieved by adding to the whole blood or red blood cell concentrates an effective amount of one or more compounds which primarily inhibit the activity of PK and secondarily inhibit the activity of DPG phosphatase and maintain those of phosphofructokinase, phosphoglycolate phosphatase and DPG mutase. Among the compounds which can be used are L-amino acids, free fatty acids, glycolytic intermediates including analogs and derivatives of phosphoenolpyruvate, and free bases, inhibitors of DPGP as well as structural analogs and derivatives of all of the above compounds. Another compound which can be used to improve the quality of stored blood is a pyrophosphate compound.

1 Claim, 3 Drawing Sheets

METHOD AND ADDITIVES FOR IMPROVING THE QUALITY AND SHELF LIFE OF STORED BLOOD

FIELD OF THE INVENTION

The present invention relates to a method for increasing quality and/or shelf life of whole blood ano red blood cell concentrates, hereafter both referred to as red cells, stored at refrigeration temperatures during usual blood banking procedures.

BACKGROUND OF THE INVENTION

The biochemical processes that occur during blood preservation or storage contribute to the diminution of the post-transfusion viability, i.e. survival of stored rec cells after transfusion to a recipient, and oxygen off-loading capacity of red cells, both of which are statistically correlated with the duration of storage period. Previous studies of stored red blood cells have indicated that intracellular levels of ATP (adenosine triphosphate) and 2,3-DPG (2,3-diphosphoglycerate) largely or entirely determine the post-transfusion viability and oxygen off-loading capabilities respectively of the red cell. It is well-established that both of these substances are products of glycolysis, a biochemical pathway that degrades glucose.

Maintenance of post-transfusion viability of stored red cells is closely correlated with the levels of cellular ATP, a high-energy compound. Glycolysis is the only ATP generated pathway in the red cell. It appears that ATP preserves membrane integrity by maintaining proper ionic gradients across the red cell membrane, adequate lipid turnover rate, hemoglobin in a functional state and normal equilibrium of oxidized and reduced glutathione, along with synthesis of adequate amounts of NAD+ and NADP+, i.e. Nicotinamide adenine dinucleotide and its phosphate.

It is well-established that oxygen off-loading ability of red cells is determined by another glycolytic intermediate, 2,3-DPG. This compound declines as a function of time during storage, most likely secondary to both a decreased rate of synthesis and an increased rate of degradation. The red cells with low 2,3-DPG show increased oxygen affinity or decreased ability to release oxygen at the tissue level. Thus, the stored red cells are less efficient vehicles of oxygen transport, the most important function of the red cells—stated otherwise, this means that stored and therefore 2,3-DPG depleted red cells are of poor quality with regard to their function.

It follows that it would be highly desirable to be able to maintain near-normal red cell 2,3-DPG and ATP as sucn a result would have profound effects in terms of both red cell function and post-transfusion survivability in vivo. Thus, adequate maintenance of both of these compounds would permit the storage of red cells for a longer period of time, which would alleviate problems of shortage of blood for transfusion and low quality of stored blood.

Previous studies of stored whole blood and stored red cell concentrates have indicated that intracellular levels of ATP and 2,3-DPG are important in extending storage capabilities. To this end, several studies have been conducted which have incorporated various chemical additives along with CPD (citrate-phosphate-dextrose) anticoagulant to stimulate glycolysis, yielding a net increase in red cell ATP level. One of the commercial additives that has recently been studied is adenine. The incorporation of adenine along with CPD anticoagulant into stored blood appears to increase ADP (adenine diphosphate) levels, thereby driving the glycolytic equilibrium toward the synthesis of ATP. However, adenine has an adverse effect on the maintenance of the level of 2,3-DPG, i.e. it lowers 2,3-DPG level with concomitant poor function of the stored red cells.

Recent concern over the levels of ATP and 2,3-DPG has become a controversial subject. Because the main objective of transfusing patients is to provide or improve the oxygen delivery to the tissues, the blood oxygen affinity, directly determined by 2,3-DPG, is of critical importance. Therefore, in providing patents with suitable blood for transfusion, one must now consider not only red cell viability in vivo but also hemoglobin oxygen affinity for adequate oxygen transport function, the ultimate goal of red cell transfusion. As a result, research has also been geared towards incorporation of chemicals into the CPD and other preservative media to increase 2,3-DPG and ATP levels.

The significance of near-normal 2,3-DPG-containing red cells becomes self-evident when one examines various clinical conditions such as congestive heart failure, right to left cardiac shunts, and hypoxemia due to pulmonary disease, where patients singularly require the oxygen transport function of the transfused red cells. The transfused red cell, totally depleted of 2,3-DPG, is said to regain half the normal level of this substance within about 24 hours, but this increase may not be rapid enough to be effective in severely ill patients. Furthermore, it is not known whether the rate of resynthesis of 2,3-DPG in the donor cells given to a critically ill patient is comparable to that observed in normal recipients. Dennis et al. (*Surgery* 77 (6):741–747, June 1975) has reported a direct correlation between the ability to compensate for low 2,3-DPG levels and the severity of the illness of the patient. Blood with nearly normal hemoglobin-oxygen affinity is thus preferable for use in massive transfusions, particularly in infants, older patients, and patients with complicating cardiovascular and pulmonary disease.

The physiological effects of high oxygen-affinity (2,3-DPG depleted) red cells on the myocardial, cerebral, hepatic, and renal functions have not yet been fully evaluated, although patients requiring massive transfusions seem to be most susceptible to the adverse effects due to very low levels of 2,3-DPG; see Beutler et al., *Vox Sang.* 20:403–413 (1970).

Although numerous investigations indicate that the levels of ATP and 2,3-DPG can be better maintained when the two chief preservative solutions ACD (acid citrate dextrose) and CPD (citrate phosphate dextrose) are supplemented with adenine, inosine, or both during storage at 4° C., this conclusion must be approached with some caution. As has been reported by Bunn et al. in *New England Journal of Medicine* 282:1414–1421 (1970), a patient receiving three or four units of thus-supplemented blood may develop hyperuricemia, which persists for approximately 24 hours. As reported by Valeri in *J. Med.* (*Basel*) 5(5):278–291 (1974), a further cause for concern is the possible renal toxicity of 2,8-dioxyadenine, a metabolite of adenine. Moreover, additives that maintain ATP level, i.e. adenine, tend to lower 2,3-DPG level and those that maintain 2,3-DPG tend to lower ATP level, thus making the maintenance of both of these compounds a currently unrealizable goal. No matter which chemical is used with an ACD or CPD preservative solution, it appears that only a combination of various chemical additives will maintain 2,3DPG levels in blood under refrigeration conditions for an acceptable period of time.

Dieindoerfer et al, in U.S. Pat. No. 3,795,581, disclose a method of storing and preserving whole blood using an aqueous solution of dihydroxyacetone to increase the 2,3-DPG content. In a later patent, 3,874,384, Deindoerfer et al disclose the use of a combination of dihydroxyacetone and ascorbic acid to maintain DPG levels in stored blood. Estep, No. 4,386,069, discloses the use of a fatty ester having at least two ester linkages comprising fatty hydrocarbon groups of from four to twelve carbon atoms each to enhance the preservation of normal red blood cell morphology during storage. Harmening, No. 4,112,070, discloses a process for extending the useful shelf life of red cells by maintaining adequate levels of ATP and 2,3-DPG by adding an insoluble polymer material as a source of inorganic phosphate ions during the storage period. Harmening-Pettiglion, No. 4,390,619, discloses a method for extending the shelf life of blood platelets by maintaining both the pH and ATP levels suitable for transfusion. This is accomplished by providing to the platelets a water-insoluble polymer containing releasable weakly basic buffer ions capable of continuously supplying buffer to the platelets.

SUMMARY OF THE INVENTION

It is, accordingly, an object of the invention to overcome deficiencies in the prior art, such as indicated above.

Another object is to provide for the improved storage of red blood cells.

Further objects are to provide a method for increasing the quality and/or shelf life of red blood cells; and to provide additives to accomplish same.

These and other objects according to the present invention are achieved by a method for improving the oxygen off-loading capacity and post-transfusion viability of whole blood and red blood cell concentrates and thereby extending the shelf life of the same stored at refrigeration temperatures or otherwise during normal blood banking. The shelf life of the blood is increased by increasing ATP and 2,3-DPG levels through manipulation (activation or inhibition) of red blood cell glycolytic and non-glycolygic enzymes during storage. This manipulation consists of inhibiting the activities of the enzymes pyruvate kinase (PK) ano 2,3-DPG phosphatase (DPGP) and activating or maintaining the activities of phosphofructokinase (PFK), 2,3-diphosphoglycerate mutase (DPGM) and phosphoglycolate phosphatase (PGP).

Inhibition of PK and activation or maintenance of DPGM constitute the major thrusts of the present invention, whereas activation or maintenance of PFK and PGP, and inhibition of DPGP constitute the secondary thrusts. The enzymes are manipulated either singly or in various combinations to optimize the maintenance of 2,3-DPG and ATP levels. The manipulation of the enzymes is brought about by using a variety of compounds which are permeable to the red blood cell membrane either naturally or under certain artificial conditions. These compounds are either known or potential effectors, i.e. activators and inhibitors of the above-mentioned enzymes. Among all the enzymes mentioned above, it has been found that the enzyme PK is strategically located in the glycolytic pathway with regard to 2,3-DpG and ATP production and therefore appears to provide a sensitive point of control to manipulate red cell glycolysis.

The location of PK in the glycolytic pathway allows for the possibility of establishing a glycolytic shuttle (a reversible glycolytic flux above tne PK step) that maintains 2,3-DPG and ATP levels by partially inhibiting the enzymatic activity of PK. A partial inhibition of PK results in phosphoenoylpyruvate (PEP) not being further catabolized. As the level of PEP builds up, it is shuttled backwards to generate 1,3-DPG which is then converted to 2,3-DPG. The biosynthesis and degradation of 2,3-DPG are normally primarily controlled by the level of 1,3-DPG (which is a function of the overall glycolytic flux) and by the activity of 2,3-DPG phosphatase (DPGP). However, a buildup of 2,3-DPG due to a partial inhibition of PK puts the level of 2,3-DPG in the position of regulating the glycolytic flux by a negative feedback. Any reduced ATP generation as a result of reduced PK activity may be overcome by driving the ATP salvage pathway through addition of adenine. Since the inhibition of PK is only partial, ATP necessary to drive the salvage pathway will be available and an oscillating glycolysis will be established in the red cell. The levels of ATP and 2,3-DPG will oscillate within normal ranges, thus preserving the viability and function of the red blood cells despite prolonged storage.

In order to potentiate the effect of inhibitors of PK, it is also desirable to manipulate other glycolytic and non-glycolytic enzymes mentioned above. The activity of DPGM in particular is directly correlated to both storage time and the level of 2,3-DPG, i.e. DPGM activity and 2,3-DPG levels decline proportionally as a function of storage period. These results indicate that the maintenance of DPGM level helps maintain 2,3-DPG level. Since PFK controls the overall glycolytic flux, and especially permits the flux above the 2,3-DPG shunt and therefore determines the level of 1,3-DPG (a precursor of 2,3-DPG), maintenance of its activity helps to maintain both 2,3-DPG and ATP levels. DPGP appears to be more active during storage due to low pH of the stored red cells and therefore a selective inhibition of the enzyme will also assist in the maintenance of 2,3-DPG levels. Lastly, an activation of PGP helps reduce the level of glycolate-2-phosphate(G-2-P), a potent activator of DPGP, ano therefore increases the 2,3-DPG level.

One of the major advantages of maintaining 2,3-DPG level by manipulation of red cell enzymes as described above is that it reduces lactic acid production by the red blood cells. This reduces lactic acidosis of the preservation medium and its inhibitory effects on glycolysis (primarily at the PFK and DPGM steps) and its detrimental effects on a number of other cellular processes. Compounds which are either known to inhibit pyruvate kinase or would be expected to do so (both experimentally and biologically) are numerous, as compared to those known to affect other above-mentioned enzymes. Some of these compounds have overlapping additive or conflicting influence on these enzymes. For these compounds to be useful in preserving blood, they must also be capable of permeating the red blood cell membrane, must be able to exert their effect preferably at low concentrations, and above all, be physiologically acceptable, so that they can be used in humans in vivo. The following Tables enumerate some of the compounds found to be useful in inhibiting PK (Table #1) and activating or inhibiting PFK, DPGM, DPGP and PGP (Table #2). Compounds that are inhibitors of PK may be classified into five groups as follows; including the concentration in the stored blood that are effective:

TABLE #1
(PK Inhibitors)

Group I: L-Amino Acids and their Derivatives and Structural analogs

| | |
|---|---|
| L-methionine | 1–10 mM |
| Methyl α-amino-isobutyric acid | 1–2 mM |
| cycloleucine | 1–2 mM |
| methylcysteine | 1–2 mM |
| ethylcysteine | 1–2 mM |
| L-alanine; L-1-aminoethyl phosphoric acid | 0.5–10 mM |
| L-phenylalanine; L-phenylalanyl methyl ester; L-1-amino-2-phenylethyl phosphoric acid | |
| L-cysteine | 1–2 mM |
| α-amino-isobutyric acid | 0.5–5 mM |

Group II: Free Fatty Acids, their Derivatives and Structural Analogs.

| | |
|---|---|
| Octoanoate | 0.2–5 mM |
| Laurate | 0.2–5 mM |
| Linoleate | 0.2–5 mM |
| Oleate | 0.2–5 mM |
| Palmitate | 0.2–5 mM |
| Myristate | 0.2–5 mM |
| Elaidate | 0.2–5 mM |

Group III: Glycolytic Intermediates and their Structural Analogs and Derivatives

| | |
|---|---|
| Phosphoenolpyruvate | 0.5–2 mM |
| D-Phospholactate | 20–50 μM |
| D-Phosphopyruvate | 0.5–2 mM |
| Phenyl pyruvate | 0.5–2 mM |
| 2-phosphoglyceric acid | 2–10 mM |
| 3-Phosphoglyceric acid | 2–10 mM |
| Phosphoglycolate | 50–100 μM |
| Phosphoglyoxylate | 50–100 μM |
| Glyoxylate | 0.5–2 mM |

Group IV: Free Bases and their mono, di and triphosphates, their Derivatives and Structural Analogs

| | |
|---|---|
| Adenosine (AMP, ADP, ATP) | 0.5–2.5 mM |
| Inosine (IMP, IDP, ITP) | 0.5–2.5 mM |
| Cytidine (CMP, CDP, CTP) | 0.5–2.5 mM |
| Thymidine (TMP, TDP, TTP) | 0.5–2.5 mM |
| Guanosine (GMP, GDP, GTP) | 0.5–2.5 mM |
| Uridine (UMP, UDP, UTP) | 0.5–2.5 mM |
| Mono- and dibutyril cAMP | 0.1–0.5 mM |
| cAMP | 0.1–0.5 mM |
| $N^6$-(Phenylisopropyl) adenosine | 10 μM |

Group V: Miscellaneous Compounds and their Derivatives and Structural Analogs

| | |
|---|---|
| Ammonia | 0.1–0.2 μM |
| Glucagon | 0.1–0.2 μM |
| Acetyl co-A and its derivatives | 30–200 μM |
| Allantoin | 1–2 mM |
| Uric acid | 1–2 mM |
| 4-ethyloxaloacetate | 10–20 μM |
| Phenethyloiguanide and its analogs | 1–2.5 mM |
| Quercetin | 10–100 μM |
| Epinephrine (± Ro 1724) | 1–20 μM |
| Copper | 0.1–2 μM |
| Phosphate, Pyrophospate | 1–20 μM |
| Fru-1, 6-diphosphate | 1–20 μM |
| Oxlate | 2-mmol |

TABLE #2
(Effectors of PFK, DPGM, DPGP and PGP)

| | | |
|---|---|---|
| Activators of PGP | Cobalt SO$_4$ | (up to 10 μM) |
| | Magnesium Chloride | (up to 10 μM) |
| | Manganese Chloride | (up to 10 μM) |
| | Nickel Sulfate | (up to 10 μM) |
| Inhibitors of DPGP | Glycerate-2-P | 50–100 μM |
| | Glycerate-3-P | 50–100 μM |

TABLE #2-continued
(Effectors of PFK, DPGM, DPGP and PGP)

| | |
|---|---|
| Glyoxylate | 50–100 μM |
| AMP, cAMP | 50–100 μM |
| Pi, PPI | 30–100 μM |
| Malonate | up to 10 mM |
| Malate | up to 5 mM |
| Maleate | up to 10 mM |
| D-Tartrate | up to 10 mM |
| L-Tartrate | up to 10 mM |
| meso-Tartrate | up to 10 mM |
| Glutamate | up to 15 mM |
| D-L-isocitrate | up to 1 mM |
| D-isocitrate | up to 1 mM |
| trans-aconitate | up to 0.5 mM |
| cis-aconitate | up to 0.20 mM |
| Pyrophosphate | up to 0.050 mM |

Presently, red blood cells stored in best available preservatiave media that have a normal survival afforded by adequate ATP levels are unable to deliver as much oxygen as are fresh red blood cells due to decreased 2,3-DPG concentrations (see FIG. #1). The present invention allows for the improved maintenance of 2,3-DPG and ATP levels during storage by using substances that are physiological and have been characterized by the FDA as being safe. These substances also will not significantly alter such blood physical characteristics as pH or flow rate.

DETAILED DESCRIPTION OF THE INVENTION

The biosynthetic and biodegradative mechanisms that control the level of 2,3-DPG during red cell storage, with special reference to the activities of glycolytic kinases and 2,3-DPG mutase as components of the synthetic pathway and 2,3-DPG phosphatase and its activator glycolate-2-phosphate (G-2-P) constituting the biodegradative pathway have been investigated. Glycolate-2-P, has been quantitated in normal human red cells, since its presence had not previously been unequivocally demonstrated, and the glycolytic enzymes, intermediates and other parameters curing prolonged red cell storage (up to 12 weeks) have been studied.

Demonstration of the Existence of Glycolate-2-P (G-2-P) in Human Red Cells

Figure 4:
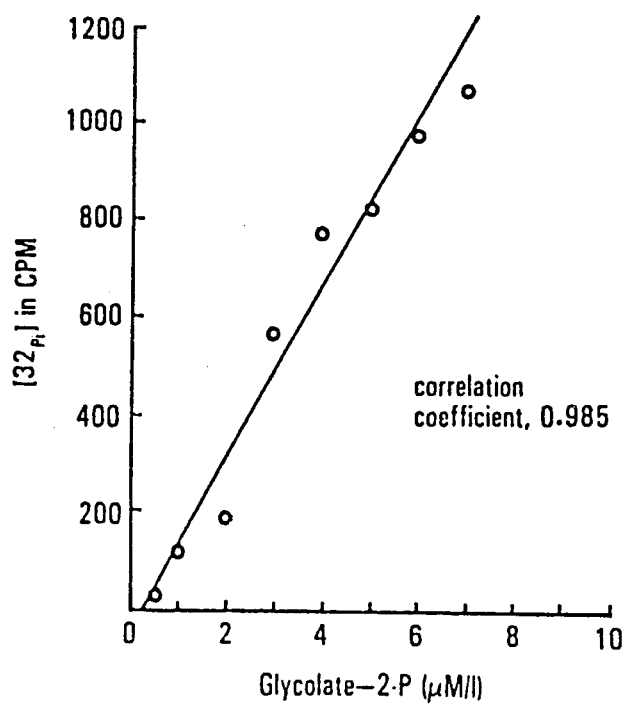
FIG. 4 shows the standard curve for the radiometric assay of glycolate-2-P.

In order to demonstrate the presence of G-2-P, which had been reported to exist at micromolar concentrations in human red cells in a single brief report, G-2-p from human red cells has now been purified and concentrated using modification of the technique described by Rose and Salon, *Biochem. Biophys. Res. Commun.* 87:869–875, 1979. The radiometric assay now developed to quantitate G-2-P is extremely sensitive and can detect as little as 50 pmole ot G-2-P (FIG. 4).

The results conclusively demonstrate that G-2-P does exist in human red cells and therefore may have a regulatory role in the maintenance of 2,3-DPG level during steady state and during red cell storage. These data, therefore, indicate that structural analogs and derivatives of G-2-P are useful as inhibitors of DPG phosphatase.

Measurements of the Key Glycolytic Enzymes and Intermediates during Storage

Figure 1:
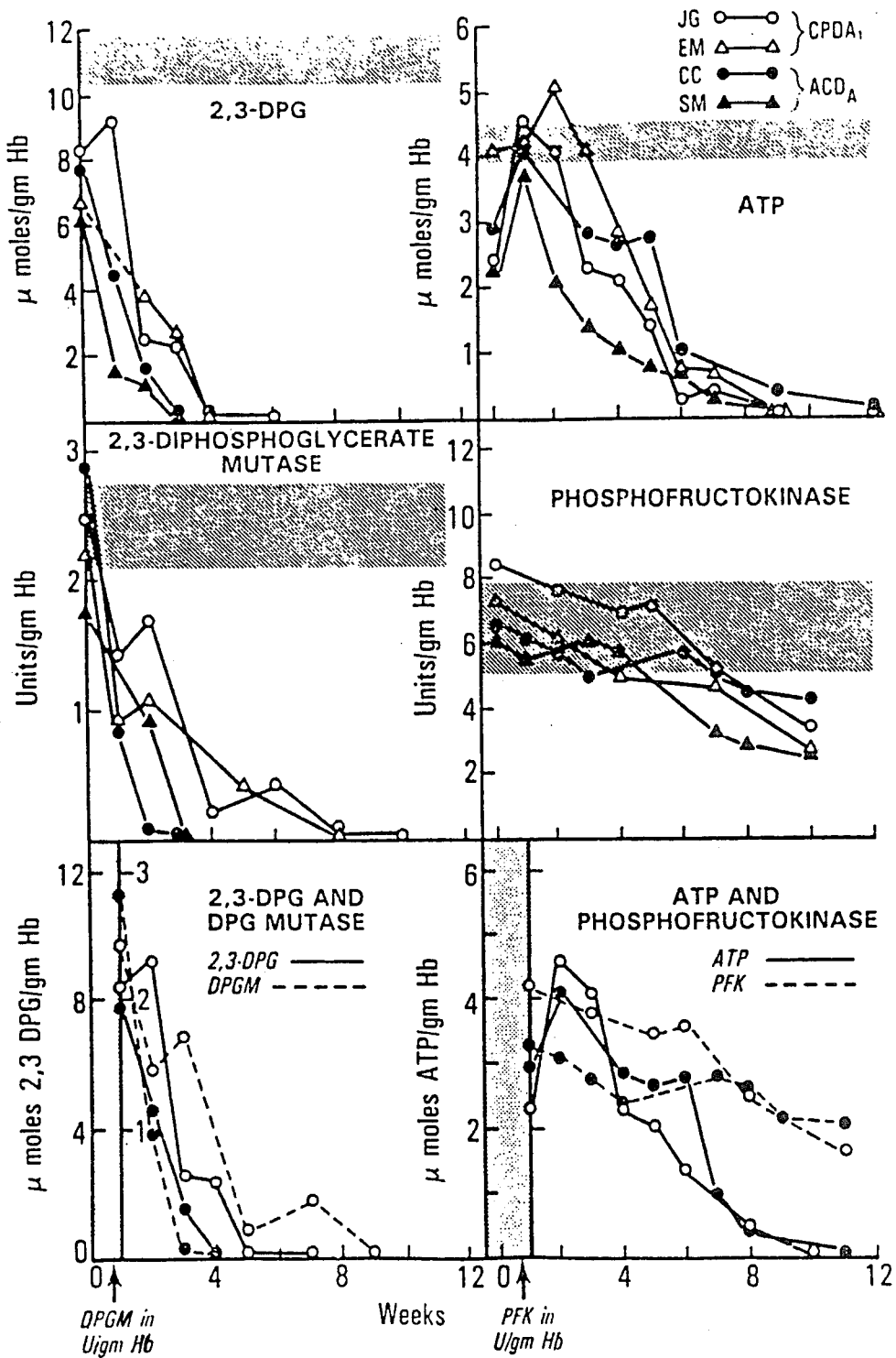
FIG. 1 shows levels of 2,3-DPG, ATP, 2,3-DPG mutase, PFK, 2,3-DPG and DPG mutase, and ATP and PFK in blood over a period of time.
Figure 2:
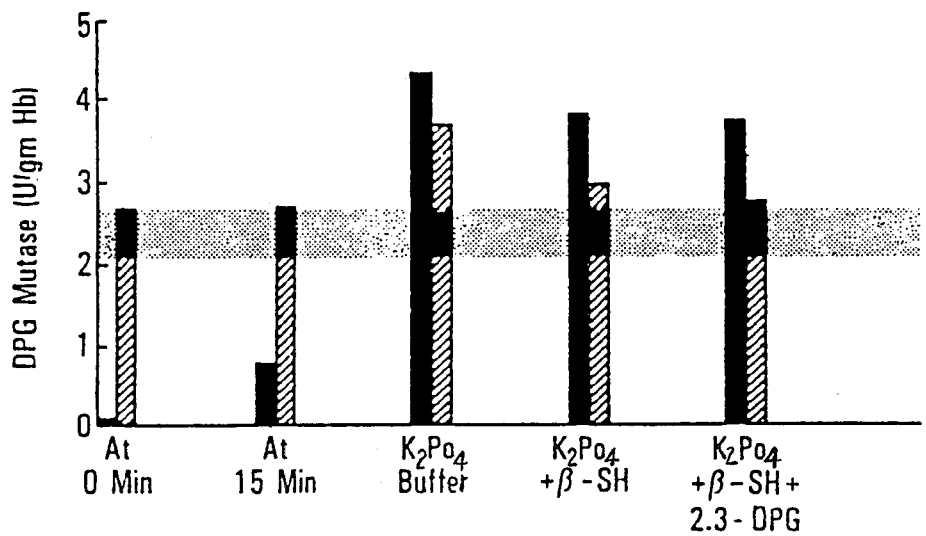
FIG. 2 shows reactivation studies of DPG mutase with different activators.
Figure 3:
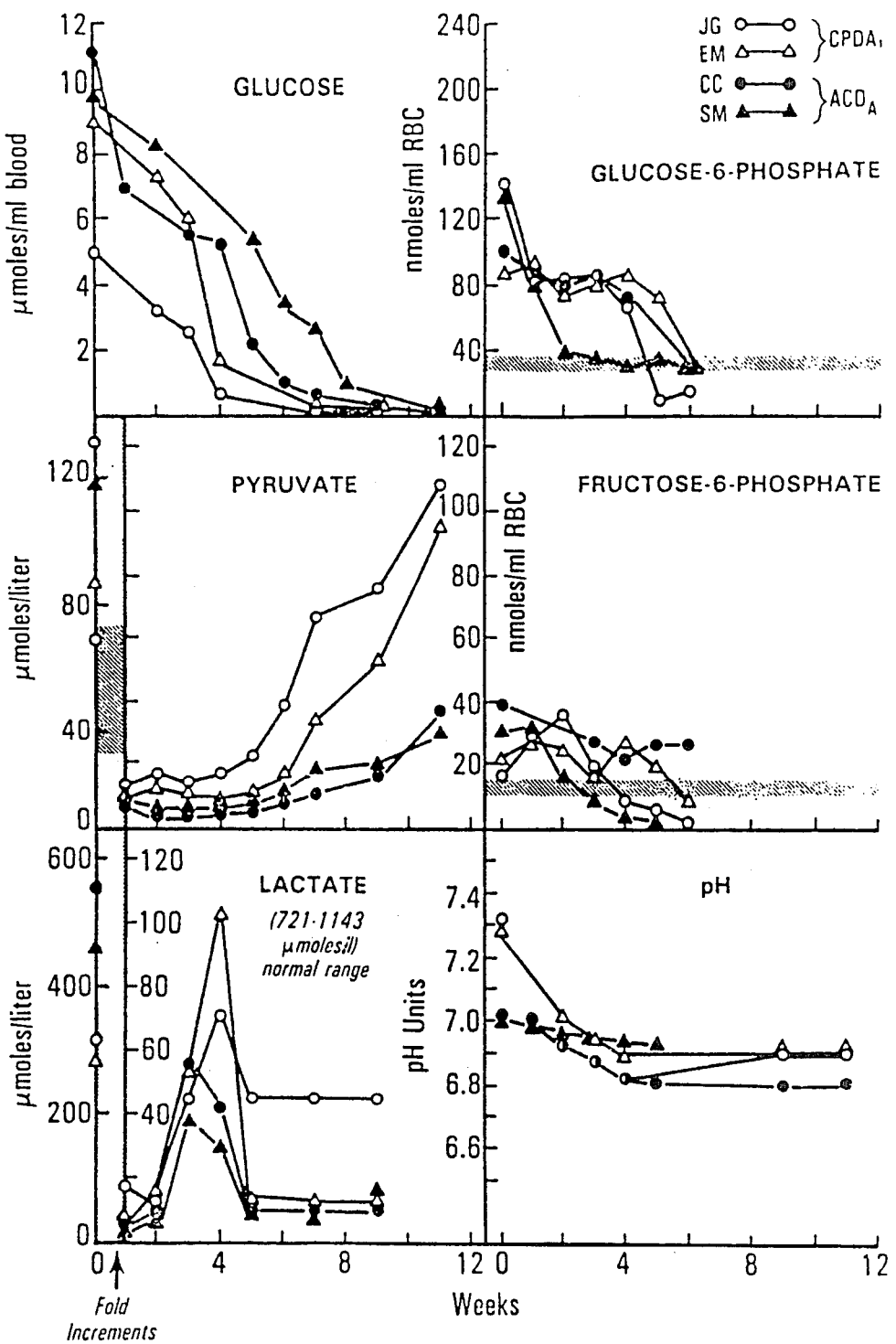
FIG. 3 shows levels of glucose, glucose-6-phosphate, pyruvate, fructose-6-phosphate, lactate, and pH in blood over a period of time.

The following red cell parameters during blood storage in ACD, CPD-$A_1$, and Adsol preservatives have now been determined: ATP, 2,3-DPG mutase, PFK, PK, HK, G-6-P, F-6-P, FDP, glucose, lactate, pyruvate, pH and free hemoglobin (FIGS. 1 and 3). The results are suggestive of the fact that 2,3-DPG mutase appears to become rate-limiting in red cell glycolysis which causes lowering of 2,3-DPG levels as a function of time (FIG. 1). The time-course of decline of 2,3-DPG mutase is essentially identical with and superimposible on that of 2,3-DPG. There has now also been observed a time-dependent activation of 2,3-DPG mutase as well as activation of the enzyme due to various activators, especially inorganic Pi (FIG. 2). Based on these results, the activity of 2,3-DPG mutase is maintained to better maintain 2,3-DPG levels.

Innhibition of Glycolytic Flux at the PK Step

It has been found that the best way to maintain higher 2,3-DPG levels was to metabolically inhibit the pyruvate kinase (PK) reaction. The method of the present invention was tested by similar studies of blood stored with L-alanine and L-phenylalanine, two potent inhibitors of PK, using a series of concentrations. The results indicate that both of these amino acids are effective in better preserving 2,3-DPG levels during blood storage. The time taken for 2,3-DPG to decline to 50% of the original value ($t_{\frac{1}{2}}$) was prolonged from 10 days (no additive) to 13-14 days (with additive). In addition, the extent of the transport of these amino acids within the red cell has been quantified under the standard procedures of blood collection, processing and preservation used currently.

Furthermore, the scientific validity of the concept has been confirmed by concurrent investigations of the blood from an individual heterozygous for PK deficiency. This individual possesses one-half normal PK activity in her red cells, and thus provides a natural model to study the effect of inhibiting the enzyme from normal blood. As expected, her red cells showed the best maintenance of 2,3-DPG levels, i.e., a $t_{\frac{1}{2}}$ of 16-17 days. Thus, it appears that if an additive can bring about—70-80% inhibition of red cell pK, it will be able to improve the quality and/or increase the shelf-life of banked blood.

A screening procedure is used to effectively test the efficacy of a number of compounds (almost all of which are physiological), that may be used as inhibitors of PK during blood banking. The assay is a modification of the procedure described by Rognstad, R. (*Biochem. Biophys. Res. Commun.* 63:900–905, 1975). The assay measures the rate of formation of $^{14}C$-pyruvate and $^{14}C$-lactate from $^{14}C$-labelled substrates providedo to the red cells which enter glycolysis above the PK step, i.e. it measures the flux at the PK step. The transport of some of these compound is facilitated by using liposomemediated transfer. Successful transfer of high concentrations of L-phenylalamine into intact red cells has been reported by this technique (Kumpathi, *J. Biochem. Biophys. Res. Commun.* 105:482, 1982).

According to the present invention, the handicaps in glycolysis that may be experienced by the red cell during storage have been determined and a method has been developed to improve the quality and shelf-life of the stored blood.

To improve the quality and prolong the shelf life of blood according to the present invention, the preserving compound(s) is either added to the bag containing the preservative into which blood is drawn directly or is added to the fresh blood or red blood cells immediately after collection into the anticoagulant. Alternatively, standard anticoagulants can be added to the blood immediately upon collection along with the preserving compound(s) of the present invention. The mixture of whole blood or red blood cells, anticoagulant and the preserving compound(s) is then stored at temperatures below 10° C., preferably at a temperature within the range of from about 1° C. to about 6° C. or lower with cryopreservative agents, e.g. glycerol.

The whole blood or red blood cells preserved according to the present invention may be stored for longer than 35 days (up to 8-10 weeks and perhaps more), while still being of as good or better quality than blood stored by standard prior art methods, such as with the use of anticoagulant acid citrate-dextrose solutions or anticoagulant citrate-phosphate-dextrose (+adenine) and Adsol solutions.

From the foregoing description and embodiments of the invention, one skilled in the art can make various changes and modifications of the invention to adapt it to various usages and conditions without departing from the spirit and scope of the invention.

What is claimed is:

1. A method for improving the quality of stored whole blood and red blood cell concentrates by manipulating red cell enzymes comprising:
    adding to the whole blood or red blood cells an effective amount of a physiologically acceptable pyrophosphate compound;
    and storing said blood.

* * * * *